United States Patent [19]
Daftary

[11] Patent Number: 5,431,567
[45] Date of Patent: Jul. 11, 1995

[54] ANATOMICAL RESTORATION DENTAL IMPLANT SYSTEM WITH INTERLOCKABLE VARIOUS SHAPED HEALING CAP ASSEMBLY AND MATCHING ABUTMENT MEMBER

[76] Inventor: Fereidoun Daftary, 50 N. La Cienega Blvd., Beverly Hills, Calif. 90211

[21] Appl. No.: 157,471

[22] Filed: Nov. 26, 1993

Related U.S. Application Data

[63] Continuation-in-part of Ser. No. 61,746, May 17, 1993, Pat. No. 5,297,963.

[51] Int. Cl.⁶ .................... A61C 13/12; A61C 13/225; A61C 8/00
[52] U.S. Cl. .................... 433/172; 433/173
[58] Field of Search ............ 433/172, 173, 174, 175, 433/176, 177

[56] References Cited

U.S. PATENT DOCUMENTS

| | | | |
|---|---|---|---|
| 4,713,004 | 12/1987 | Linkow et al. | 433/174 |
| 4,856,994 | 8/1989 | Lazzara et al. | 433/173 |
| 4,872,840 | 10/1989 | Bori | 433/173 |
| 5,035,619 | 7/1991 | Daftary | 433/173 |
| 5,052,929 | 10/1991 | Seal | 433/173 |
| 5,073,111 | 12/1991 | Daftary | 433/173 |
| 5,125,841 | 6/1992 | Carlsson et al. | 433/172 X |
| 5,145,372 | 9/1992 | Daftary et al. | 433/173 |
| 5,169,308 | 12/1992 | Kuist | 433/172 X |
| 5,213,502 | 5/1993 | Daftary | 433/172 |
| 5,246,370 | 9/1993 | Coatoam | 433/173 |
| 5,254,005 | 10/1993 | Zuest | 433/173 |
| 5,286,195 | 2/1994 | Clostermann | 433/172 |
| 5,297,963 | 3/1994 | Daftary | 433/172 |

*Primary Examiner*—Nicholas D. Lucchesi
*Attorney, Agent, or Firm*—Thomas I. Rozsa; Tony D. Chen

[57] ABSTRACT

The present invention is an anatomical restoration dental implant system with an interlockable various shaped healing cap assembly and a matching abutment member. The healing cap assembly includes an integral bolt member which has a widened head segment and an elongated shaft segment. The healing cap assembly also includes a healing cap member which has a divergent body with a larger rounded triangle shaped end. The healing cap member also has a stepped interior bore with threaded section offset from that of the bolt member so that the healing cap member and the bolt member are interlockable. The present invention also comprises a matching abutment member for supporting a tooth analog with a rounded triangle shaped root. The abutment member has a bolt segment which is identical to the bolt member of the healing cap assembly, and a frusto-conical shaped head segment. The large end of the frusto-conical shaped head segment of the abutment member is circular shaped and smaller than the rounded triangle shaped end of the healing cap member, such that when the abutment member is attached to the healing cap member, a rounded triangle shaped shoulder is created for matching perfectly with the rounded triangle shaped root of the tooth analog.

29 Claims, 7 Drawing Sheets

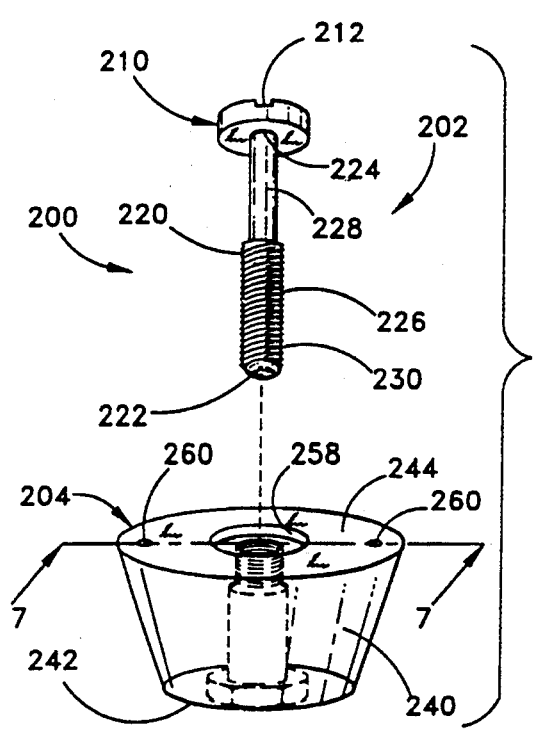
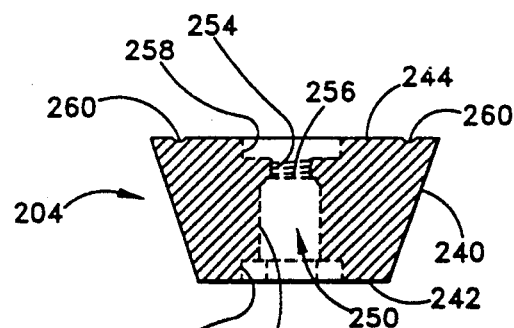
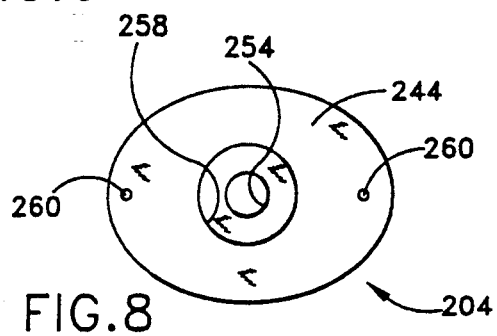
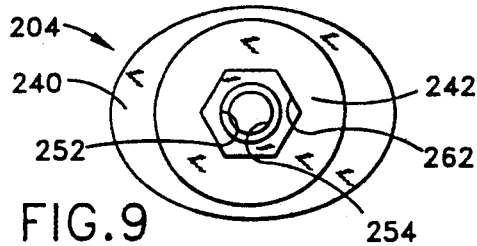
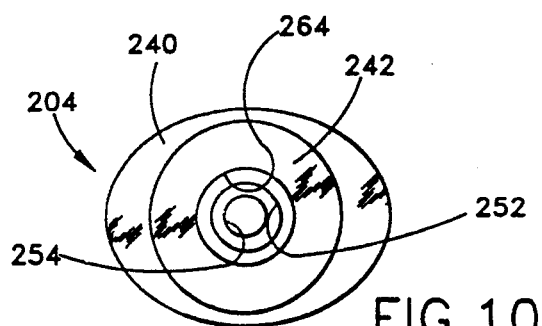
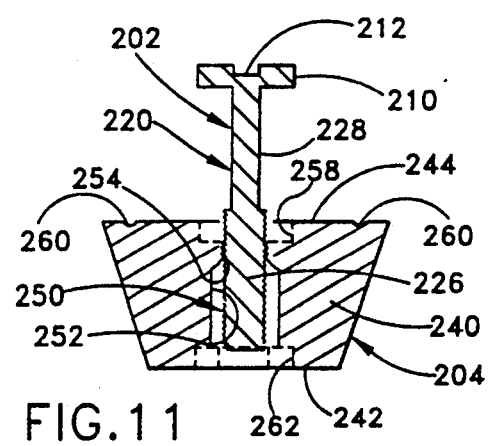
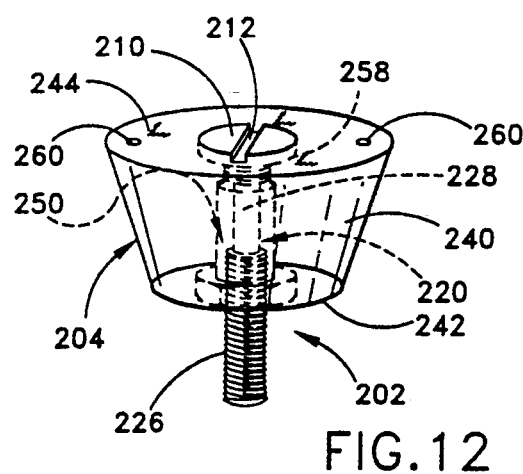

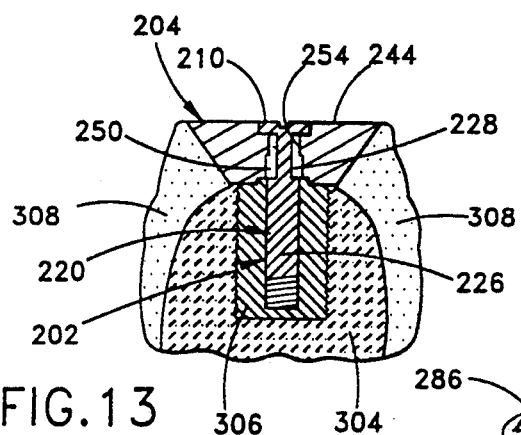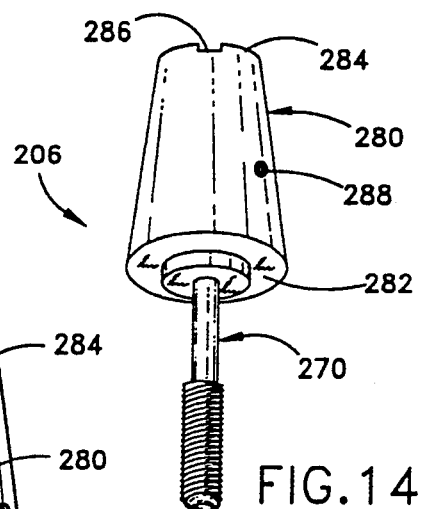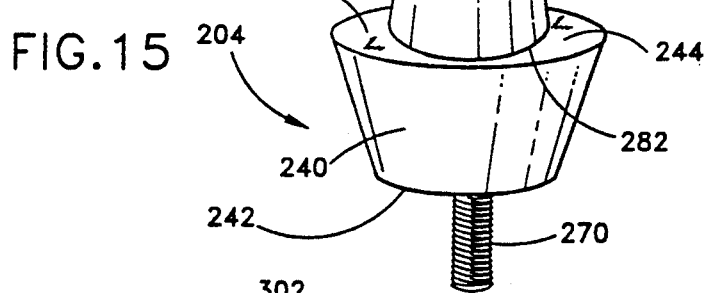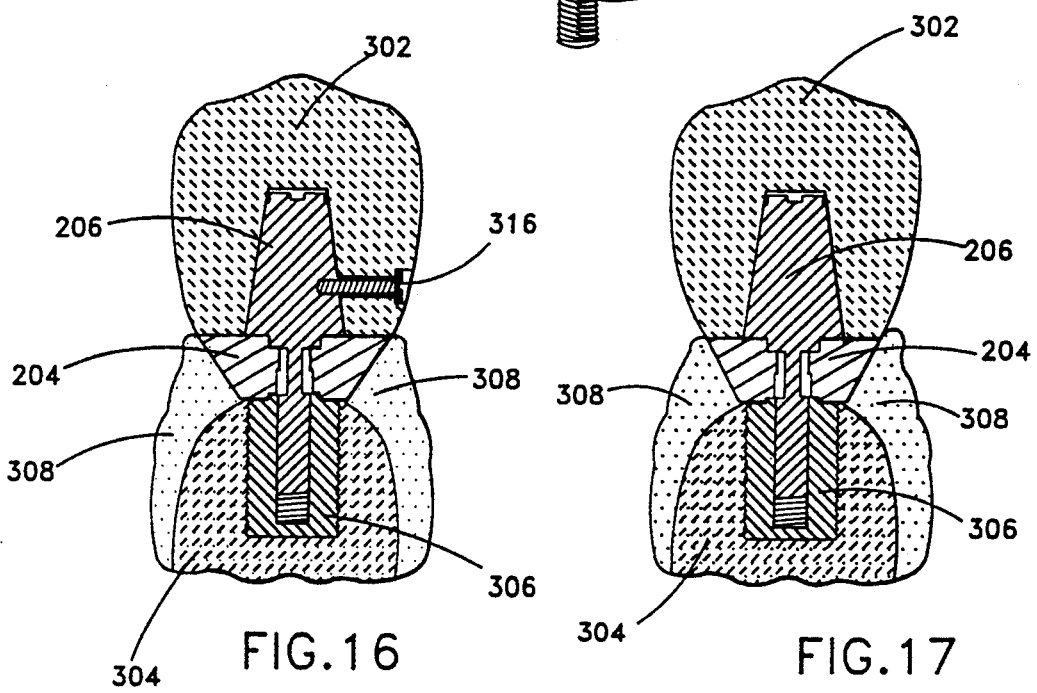
FIG.13  FIG.14  FIG.15  FIG.16  FIG.17

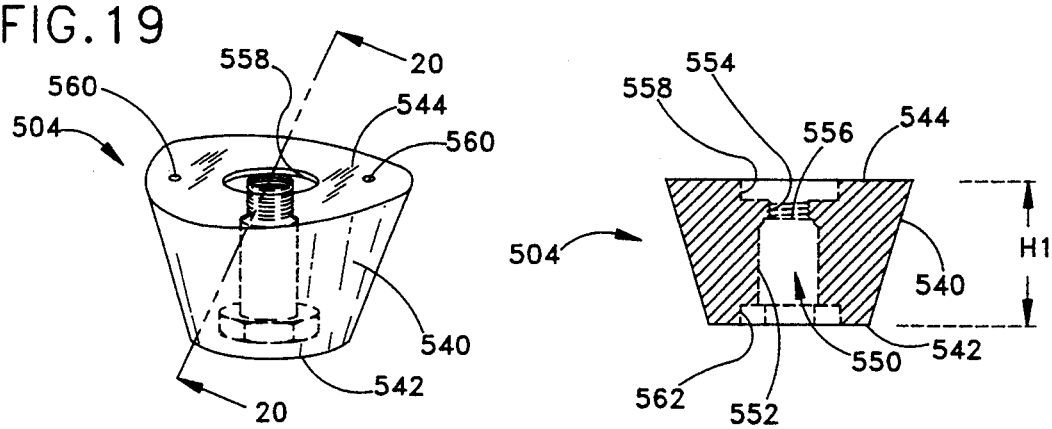
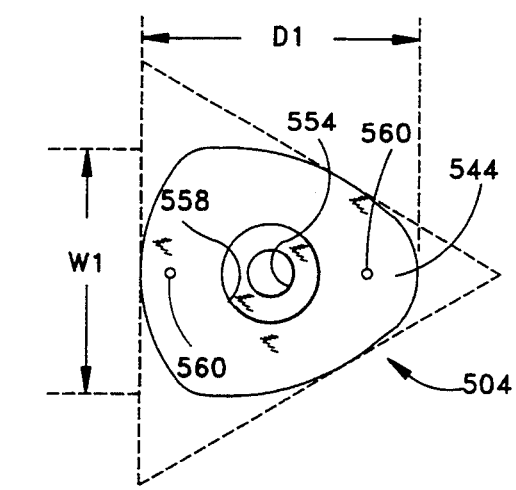
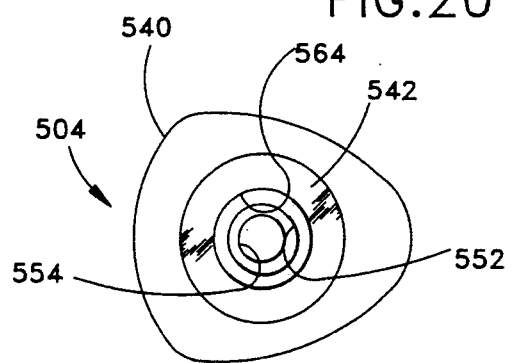
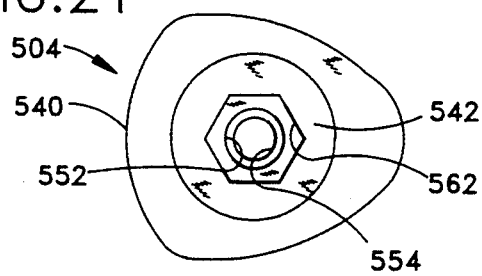
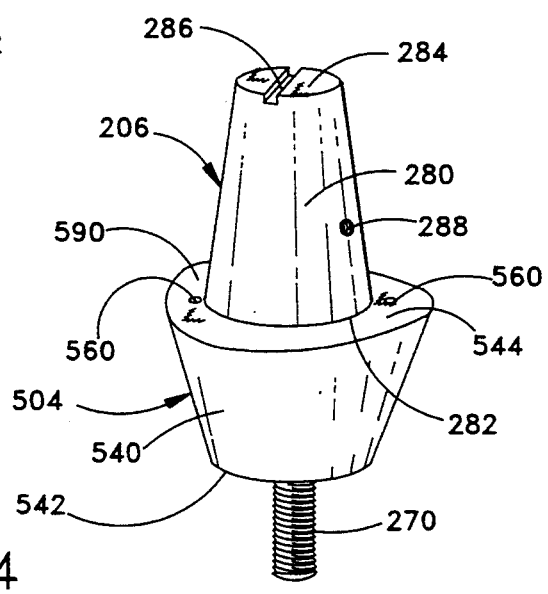

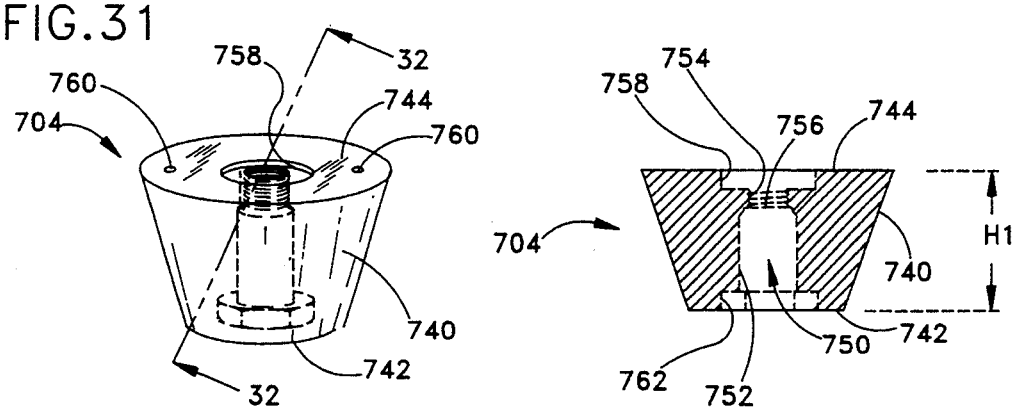
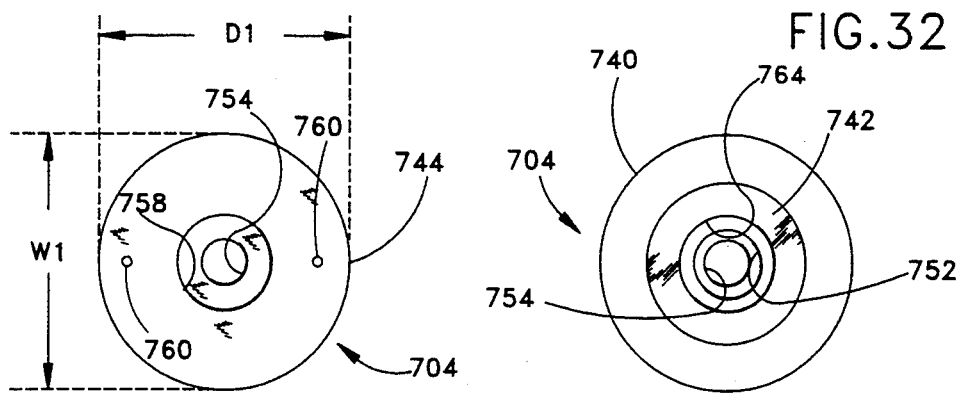
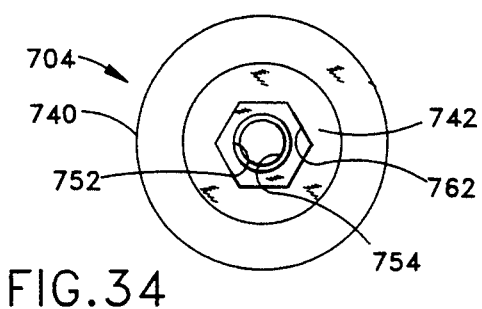
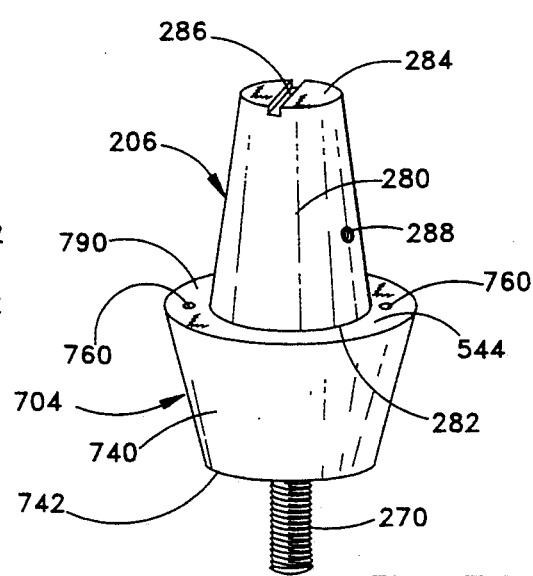

ANATOMICAL RESTORATION DENTAL IMPLANT SYSTEM WITH INTERLOCKABLE VARIOUS SHAPED HEALING CAP ASSEMBLY AND MATCHING ABUTMENT MEMBER

BACKGROUND OF THE INVENTION

This application is a Continuation-in-part of patent application Ser. No. 08/061,746 filed May 17, 1993 (hereafter "the '746 Application"), now U.S. Pat. No. 5,297,963.

FIELD OF THE INVENTION

The present invention relates generally to the field of dental implants and in particular to a system providing a tooth analogue and a gingival tissue healing cap which results in a restoration having tissue-implant profiles similar to that of a natural tooth and its surrounding gingiva. The present invention also relates to fitting a tooth with a temporary crown and final prosthesis after the initial implant structure has been inserted and the surrounding tissue has healed. More particularly, the present invention relates to the field of anatomical restoration dental implant systems with interlockable various shaped healing cap and abutment.

DESCRIPTION OF THE PRIOR ART

Many systems have been proposed for rigidly fixing metal or ceramic materials to the alveolus of a human mandible or maxilla in an effort to provide a long term replacement for lost teeth. Early systems were successful for only limited periods of time and were eventually rejected as foreign bodies. Later systems, as described by U.S. Pat. Nos. 3,589,011 to Sneer, 3,797,113 to Brainin, 3,979,828 to Taylor, 4,324,550 to Reuther et al., and 4,416,679 to Mozsary et al., have proven to offer long term success by providing rigid anchorage in the supporting bone. Intraoral restoration of such ossointegrated devices has been accomplished with many different systems that modified the original attempts. Such modifications have been described in U.S. Pat. Nos. 4,780,080 to Harras, 4,713,003 to Symington et al., and 4,657,510 to Gittlemen. However, these restorative systems have required biologic and aesthetic compromises. The interface between an implant and its surrounding gingival tissue is often insufficiently close to prevent food and bacteria from entering this area. Such foreign matter can cause chronic infection and bone loss, resulting in eventual loss of the implant. Implants in current use have a round root form dimensionally different from that of a normal tooth root morphology. This makes aesthetic restoration difficult and impedes the development of a natural soft gingival tissue contour.

The inventor and applicant of the present invention has been practicing anatomical restoration dental implant surgeries for many years and is the patentee of a series U.S. Patents related to anatomical restoration dental implant systems. U.S. Pat. No. 5,073,111 issued to Daftary on Dec. 17, 1991 (hereafter "the '111 Patent") disclosed an anatomical restoration dental implant system. Shown in FIGS. 1 and 2, the '111 Patent disclosed an anatomical restoration dental implant system for implanting a tooth analogue 102 in the alveolus of the jawbone 104. The system comprises an implantable fixture 106 implanted through opened gingival tissue 108 into the alveolus of the jaw bone 104. A cover screw (not shown) is used for sealing the hollow of the implant fixture 106 during the time the jaw bone 104 is growing about the implant fixture 106. After osseointegration of the implant fixture 106, the gingiva 108 is reopened and the cover screw is removed and replaced by a healing cap 110. The healing cap 110 provides a predetermined contour to the re-healing gingival tissue 108. After the re-opened gingival tissue 108 has healed about the healing cap 110, the healing cap 110 is removed and replaced with an abutment 112 having the same contour as that of the healing cap 110. Having the same contour permits the abutment 112 to tightly fit the healed opening in the gingival tissue 108 upon engagement of the abutment 112 with the implant fixture 106. The abutment 112 is removably affixed to the implant fixture 106 by a screw 114. Thereafter the tooth analogue 102 is releasibly engagable with the abutment 112 by a small holding screw 116.

U.S. Pat. No. 5,035,619 issued to Daftary on Jul. 30, 1991 (hereafter "the '619 Patent") disclosed an anatomical restoration dental implant system with improved healing cap and abutment. U.S. Pat. No. 5,145,372 issued to Daftary et al. on Sep. 8, 1992 (hereafter "the '372 Patent") disclosed an anatomical restoration dental implant system with reinforced healing cap and abutment. The '619 Patent introduced an assembly of a two-piece healing cap and a matching abutment for improving the healing process of the gingival tissue 108, and the '372 Patent provided a reinforced assembly of the two-piece healing cap and the matching abutment. The two-piece healing cap configurations are designed to prevent the unnecessary damage or delay to the healing of the gingival tissues.

It is always desirable to improve the anatomical restoration dental implant system so that it can provide a contour more nearly approximating that of a natural tooth and its surrounding tissue, and an implant root and gingival tissue interface that enhances the resistance to bacterial infection.

SUMMARY OF THE INVENTION

The present invention is an anatomical restoration dental implant system with an interlockable various shaped healing cap assembly and a matching abutment member.

It is known that one of the common features of all existing anatomical restoration dental implant systems, including the '111 Patent, the '619 Patent and the '372 Patent, is that once the abutment 112 is in place, it provides a circular shoulder 118 around the abutment 112 for a tooth analogue 102. In practicing anatomical restoration dental implant surgeries, the inventor of the present invention has discovered that, when the root of the tooth analogue is oval or elliptical instead of round or circular, it will not match perfectly with the circular shoulder around the abutment. As shown in FIG. 3, when the bottom end or root of the tooth analogue 102 is elliptical, it will not fully cover the circular shoulder 118. In other words, the bottom end surface of the tooth analogue 102 is often not a perfect circle but an ellipse. While the diameter A of the long-axis of the ellipse is matching the diameter D of the circular shoulder 118, the diameter B of the short-axis of the ellipse is not. The result of this mismatching is shown in FIG. 4, which is observed at a 90 degree angle from that of FIG. 3. As shown in FIGS. 3 and 4, there will be two opposite narrow spaces 120 left between the tooth analogue 102 and the gingival tissues 108. This creates a serious problem because it will take a long period of time for the gingival tissues 108 to recover and heal around the tooth analogue 102 to fill the two narrow spaces, and meanwhile food debris and bacteria may be collected within the spaces, which in turn will impede the complete healing of the gingival tissues and increases the chance of causing infectious diseases.

Another problem presented by the mismatch is shown in FIG. 5, which is an illustrative diagram of a patient's oral cavity. Suppose two tooth analogues 122 and 124 are going to be positioned next to each other between the patient's tongue 126 and the interior surface 128 of the patient's cheek. The profile of the bottom surface of the tooth analogues is elliptical. According to the orientation of the natural tooth, the long-axis of the ellipse is aligned with the general radius direction of the patient's oval cavity. Dotted circle 132 shows the profile of the circular shoulder around the abutment for supporting tooth analogue 122, and dotted circle 134 shows the profile of the circular shoulder around the abutment for supporting tooth analogue 124. It can be seen that the larger profile of the circular shoulders will prevent the two tooth analogues 122 and 124 from being positioned at a desired or required close distance because the circular shoulders around the abutments for supporting the two tooth analogues 122 and 124 will interfere with each other.

It has been discovered, according to the present invention, that if a new healing cap with oral or elliptical shaped top surface is utilized with the abutment, then the shoulder around the abutment is elliptical which will perfectly match with the oval root of the tooth analogue. Therefore, it is a primary object of the present invention to provide a healing cap with an elliptical top surface for providing an elliptical shoulder around the abutment, so that there can be a perfect match between the elliptical root of a tooth analogue and the abutment shoulder.

As shown in FIG. 1, in the prior art when the top of the healing cap 110 is round, it does not matter how it is oriented. Thus the healing cap 110 can be simply threaded to the implant fixture 106 until they are fully engaged. However, for the new healing cap with elliptical top, it must be oriented in the way shown in FIG. 5, that is, the long-axis of the ellipse must be aligned with the general radius direction of the patient's oval cavity. Consequently the new healing cap must have no threaded relationship with the implant fixture 106. In other words, the angle of the new healing cap must be adjustable when it is attached to the implant fixture 106.

Therefore, it is also an object of the present invention to provide a separate bolt for securing the new elliptical healing cap to the implant fixture which allows the adjustment of the orientation of the elliptical healing cap. Accordingly, the present invention is an anatomical restoration dental implant system with an elliptical healing cap assembly and matching abutment member. The present invention elliptical healing cap assembly includes an elliptical healing cap member and a separate bolt member. The bolt member extends through a central bore of the healing cap member, and has screw threads so that it can be threadedly engaged with the implant fixture to tightly secure the elliptical healing cap member to the implant fixture.

It has been discovered, according to the present invention, that it will be desirable to make the healing cap and the bolt not only separable, but also interlockable. Making the two pieces of the healing cap assembly interlockable can prevent mismatching the pieces of different healing caps, ease the effort of aligning the two pieces in a patient's oral cavity, and reduce the chance of losing the small bolt in the patient's oral cavity.

It has also been discovered, according to the present invention, that if instead of having a smooth bore, the healing cap member of the elliptical healing cap assembly has a central bore with screw threads, then when the bolt member of the of the elliptical healing cap assembly is extended through the central bore of the healing cap member, the bolt member can be threadedly engaged with the healing cap member so that they are interlocked with each other.

However, it has further been discovered, according to the present invention, that if the bolt member is threadedly engaged with both the healing cap member and the implant fixture, then the threaded relationship between the healing cap member and the bolt member will prevent the adjustment of the orientation of the healing cap member when the bolt member is tightened to the implant fixture. This is because there are three interconnections or cross-engagements between the three pieces, i.e., the healing cap member, the bolt member and the implant fixture. The bolt member is threadedly engaged with both the healing cap member and the implant fixture. On the one hand, when the bolt member has a threaded relationship with the healing cap member, it applies not only a translational downward force but also a rotational torque to the healing cap member. The translational force will act to fasten the healing cap to the implant fixture, but the rotational torque will act to rotate the healing cap about the implant fixture. Therefore, if the bolt member is simultaneously threadedly engaged with both the implant fixture and the healing cap member, then the latter engagement will act to change the orientation of the elliptical healing cap member. This is impermissible because the orientation of the elliptical healing cap must be kept unchanged, so that the long-axis of the elliptical healing cap member is aligned with the general radius direction of the patient's oral cavity.

It has additionally been discovered, according to the present invention, that if the bolt member is divided into two sections including an upper smooth section and a lower threaded section, and alternatively the central bore of the healing cap member is divided into two sections including an upper threaded section and a lower smooth section which are opposite to two sections of the bolt member, then when the bolt member is initially extended into the central bore of the healing cap member from the upper end of the healing cap member, the lower threaded section of the bolt member will threadedly engage with the upper threaded section of the healing cap member. However, when the bolt member is further extended into the central bore of the healing cap member, the lower threaded section of the bolt member will disengage from the upper threaded section of the healing cap member and align with the lower smooth section of the healing cap member, and there will no longer be a threaded relationship between the bolt member and the healing cap member because their respective threaded portions are offset from each other. Therefore, since the bolt member is threadedly engaged with the implant fixture and it is no longer threadedly engaged with the healing cap member, there is no action or force from the bolt member to rotate the healing cap member. Thereafter the lower threaded section of the bolt member can be threaded into the fixture to secure the healing cap thereon.

It has also been discovered, according to the present invention, that if the matching abutment member has a lower bolt portion which is identical to the bolt member of the elliptical healing cap assembly, then it can be attached to the healing cap member by simply replacing the bolt member, and the attachment of the abutment member will not have any effect on the orientation of the healing cap member because when the abutment member is threadedly engaged with the implant fixture, it is no longer threadedly engaged with the healing cap member.

It is therefore another primary object of the present invention to provide an interlockable elliptical healing cap assembly for anatomical restorative dental implant systems. The interlockable feature of the present invention healing cap assembly will prevent the pieces of different healing caps from being mismatched, ease the difficulty of alignment of the two pieces in a patient's oral cavity, and reduce the chance of dropping the bolt member into the patient's oral cavity.

It is also an object of the present invention to provide an interlockable elliptical healing cap assembly for anatomical restorative dental implant systems, where the central bore of the healing cap member has inner screw threads engagable with the outer screw threads of the bolt member, so that the healing cap member and the bolt member can be threadedly engaged and thereby interlocked.

It is a further object of the present invention to provide an interlockable elliptical healing cap assembly for anatomical restorative dental implant systems, where the healing cap member is only threadedly engaged with the bolt member when the bolt member has not yet threadedly engaged with the implant fixture. When the bolt member is threadedly engaged with the implant fixture, the healing cap member is no longer threadedly engaged with the bolt member to allow the adjustment of the orientation of the healing cap member.

It is an additional object of the present invention to provide an interlockable elliptical healing cap assembly for anatomical restorative dental implant systems, where the bolt member has an upper smooth section and a lower threaded section, and the central bore of the healing cap member has alternatively an upper threaded section and a lower smooth section. This design offsets the threaded portions of the two interlockable members.

When the bolt member is initially extended into the central bore of the healing cap member from the upper end of the healing cap member, the lower threaded section of the bolt member will threadedly engage with the upper threaded section of the healing cap member. When the bolt member is further extended into the central bore of the healing cap member, the lower threaded section of the bolt member will disengage from the upper threaded section of the healing cap member and align with the lower smooth section of the healing cap member, and there will no longer be a threaded relationship between the bolt member and the healing cap member because their respective threaded portions are offset from each other. Therefore, since the bolt member is threadedly engaged with the implant fixture and it is no longer threadedly engaged with the healing cap member, there is no action or force from the bolt member to rotate the healing cap member. Thereafter the lower threaded section of the bolt member can be threaded into the fixture to secure the healing cap thereupon.

It is another object of the present invention to provide a matching abutment member having a lower bolt portion that is identical to the bolt member of the elliptical healing cap assembly, so that it can be attached to the healing cap member by simply replacing the bolt member without altering the orientation of the healing cap member, since once the abutment member is threadedly engaged with the implant fixture, it is no longer threadedly engaged with the healing cap member.

The present invention comprises an interlockable elliptical healing cap assembly attachable to an anatomical restoration dental implant fixture which is embedded into a patient's jawbone and has an exposed end having a hollow portion with inner screw threads. The healing cap assembly includes an integral bolt member which has a widened head segment and an elongated shaft segment, where the shaft segment has a proximal section with screw threads and a smooth distal section. The healing cap assembly further includes a healing cap member which has a divergent body with a smaller proximal end, a larger distal end, and a stepped interior bore extending from the distal end to the proximal end, where the larger distal end is elliptical shaped and has a long-axis and a short axis, and the interior bore has a smooth proximal section and a threaded distal section. The healing cap member and the bolt member are interlockable by threading the proximal section of the shaft segment of the bolt member into the distal section of the interior bore of the healing cap member. The present invention also comprises a matching abutment member for supporting a tooth analogue with an elliptical root. The abutment member has a proximal bolt segment which is identical to the bolt member of the healing cap assembly, and a distal frusto-conical shaped head segment which has a larger proximal end integrally connected to the proximal bolt segment, and a smaller distal end with means for adapting a driving tool. The large proximal end of the abutment member is circular shaped and has a diameter smaller than the short-axis of the elliptical shaped distal end of the healing cap member, such that when the abutment member is attached to the healing cap member in replacement of the bolt member for supporting the tooth analogue, an elliptical shoulder is created for matching the elliptical root of the tooth analogue.

It has been additionally discovered, according to the present invention, that in addition to the oval and round shaped healing caps, other shaped healing caps are also needed to better fit with the root of a tooth analogue. As shown in FIG. 18, tooth are different. The names of the teeth are listed in TABLE ONE.

It can be seen from FIG. 18 that the roots of the molars are generally round shaped, accordingly the round shaped healing caps are suitable for the molars. It can also be seen that the roots of the bicuspids and cuspids are generally elliptical shaped, accordingly the elliptical healing cap assemblies disclosed in the '746 Application are suitable for the bicuspids.

TABLE ONE

| | |
|---|---|
| 411 | Upper right Central incisors |
| 412 | Upper right Lateral incisors |
| 413 | Upper right Cuspids (eye tooth) |
| 414 | Upper right First bicuspid |
| 415 | Upper right Second bicuspid |
| 416 | Upper right First molar |
| 417 | Upper right Second molar |

TABLE ONE-continued

| | |
|---|---|
| 418 | Upper right Third molar (wisdom tooth) |
| 421 | Upper left Central incisors |
| 422 | Upper left Lateral incisors |
| 423 | Upper left Cuspids (eye tooth) |
| 424 | Upper left First bicuspid |
| 425 | Upper left Second bicuspid |
| 426 | Upper left First molar |
| 427 | Upper left Second molar |
| 428 | Upper left Third molar (wisdom tooth) |
| 431 | Lower right Central incisors |
| 432 | Lower right Lateral incisors |
| 433 | Lower right Cuspids (eye tooth) |
| 434 | Lower right First bicuspid |
| 435 | Lower right Second bicuspid |
| 436 | Lower right First molar |
| 437 | Lower right Second molar |
| 438 | Lower right Third molar (wisdom tooth) |
| 441 | Lower left Central incisors |
| 442 | Lower left Lateral incisors |
| 443 | Lower left Cuspids (eye tooth) |
| 444 | Lower left First bicuspid |
| 445 | Lower left Second bicuspid |
| 446 | Lower left First molar |
| 447 | Lower left Second molar |
| 448 | Lower left Third molar (wisdom tooth) |

However, it can be seen from FIG. 18 that the root of the incisors are generally rounded triangular shaped. More particularly, the roots of the two upper central incisors 411 and 421 are more rounded equilateral triangle shaped, whereas the two upper lateral incisors 412 and 422 and the four lower incisors 431, 432, 441 and 442 are more rounded isosceles triangular shaped. Therefore, the conventional round shaped healing caps or the elliptical healing cap assemblies disclosed in the '746 Application cannot closely fit with the root of the tooth analogues of the incisors.

It is therefore a further object of the present invention to provide healing caps with various shaped top surfaces, which can provide a better match with the various shaped tooth analogues, particularly the incisor analogues which have rounded triangular shaped roots.

The present invention also comprises an interlockable healing cap assembly attachable to an anatomical restoration dental implant fixture which is embedded into a patient's jawbone and has an exposed end having a hollow portion with inner screw threads. The healing cap assembly comprises an integral bolt member having a widened head segment and an elongated shaft segment, the shaft segment having a proximal section with screw threads and a smooth distal section. It also comprises a healing cap member having a divergent body with a smaller proximal end, a larger distal end, and a stepped interior bore extending from the distal end to the proximal end, the larger distal end having a rounded triangle shape, and the interior bore having a smooth proximal section and a threaded distal section. The healing cap member and the bolt member are interlockable by threading the proximal section of the shaft segment of the bolt member into the distal section of the interior bore of the healing cap member. The distal section of the shaft segment of the bolt member is longer than the distal section of the interior bore of the healing cap member, such that after the proximal section of the shaft segment of the bolt member is completely threaded through the distal section of the interior bore of the healing cap member from the distal end of the healing cap member, the healing cap member and the bolt member are no longer threadably engaged. The shaft segment of the bolt member is longer than the interior bore of the healing cap member, such that after the shaft segment of the bolt member extends through the interior bore of the healing cap member from the distal end of the healing cap member, there is still a substantial portion of the proximal section of the shaft segment of the bolt member which can be threadably engaged with the implant fixture for fastening the healing cap member to the exposed end of the implant fixture.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 6 is a perspective view of the present invention interlockable elliptical healing cap assembly, including an elliptical healing cap member and a bolt member.

FIG. 7 is a cross-sectional view of the elliptical healing cap member of the present invention interlockable elliptical healing cap assembly.

FIG. 8 is a top view of the elliptical healing cap member of the present invention interlockable elliptical healing cap assembly.

FIG. 9 is a bottom view of the elliptical healing cap member of the present invention interlockable elliptical healing cap assembly, showing a hexagonal recess for matching with a complementary hexagonal lip on the implant fixture.

FIG. 10 is a bottom view of an alternative embodiment of the elliptical healing cap member of the present invention interlockable elliptical healing cap assembly, showing a round recess for matching with a complementary circular lip on the implant fixture.

FIG. 11 is a cross-sectional view showing the interlockable feature of the elliptical healing cap member and the bolt member of the present invention interlockable elliptical healing cap assembly.

FIG. 12 is a perspective view showing the present invention interlockable elliptical healing cap assembly.

FIG. 13 is a cross-sectional view of the present invention anatomical restoration dental implant system, showing the elliptical healing cap member secured onto the implant fixture by the bolt member.

FIG. 14 is a perspective view of the present invention abutment member which matches the elliptical healing cap member of the present invention interlockable elliptical healing cap assembly.

FIG. 15 is a perspective view of the abutment member attached to the elliptical healing cap member of the present invention interlockable elliptical healing cap assembly.

FIG. 16 is a cross-sectional view of the present invention anatomical restoration dental implant system, showing the matching abutment member which is secured on the elliptical healing cap member for supporting a tooth analogue.

FIG. 17 is also a cross-sectional view of the present invention anatomical restoration dental implant system, observed at a 90 degree angle from that of FIG. 16, showing that no space is left between the tooth analogue and the gingival tissues because of the perfect matching between the elliptical root of the tooth analogue and the circular shoulder around the abutment.

FIG. 19 is a perspective view of the rounded equilateral triangle shaped healing cap member of the present invention interlockable healing cap assembly.

FIG. 20 is a cross-sectional view of the rounded equilateral triangle shaped healing cap member of the present invention interlockable healing cap assembly.

FIG. 21 is a top view of the rounded equilateral triangle shaped healing cap member of the present invention interlockable healing cap assembly.

FIG. 22 is a bottom view of the rounded equilateral triangle shaped healing cap member of the present invention interlockable healing cap assembly, showing a hexagonal recess for matching with a complementary hexagonal lip on the implant fixture.

FIG. 23 is a bottom view of an alternative embodiment of the rounded equilateral triangle shaped healing cap member of the present invention interlockable healing cap assembly, showing a round recess for matching with a complementary circular lip on the implant fixture.

FIG. 24 is a perspective view of the abutment member attached to the rounded equilateral triangle shaped healing cap member of the present invention interlockable healing cap assembly.

FIG. 31 is a perspective view of a rounded shaped, in particular a circular shaped, healing cap member of the present invention interlockable healing cap assembly.

FIG. 32 is a cross-sectional view of the circular shaped healing cap member of the present invention interlockable healing cap assembly.

FIG. 33 is a top view of the circular shaped healing cap member of the present invention interlockable healing cap assembly.

FIG. 34 is a bottom view of the circular shaped healing cap member of the present invention interlockable healing cap assembly, showing a hexagonal recess for matching with a complementary hexagonal lip on the implant fixture.

FIG. 35 is a bottom view of an alternative embodiment of the circular shaped healing cap member of the present invention interlockable healing cap assembly, showing a round recess for matching with a complementary circular lip on the implant fixture.

FIG. 36 is a perspective view of the abutment member attached to the circular shaped healing cap member of the present invention interlockable healing cap assembly.

DESCRIPTION OF THE PREFERRED EMBODIMENT

Figure 1:
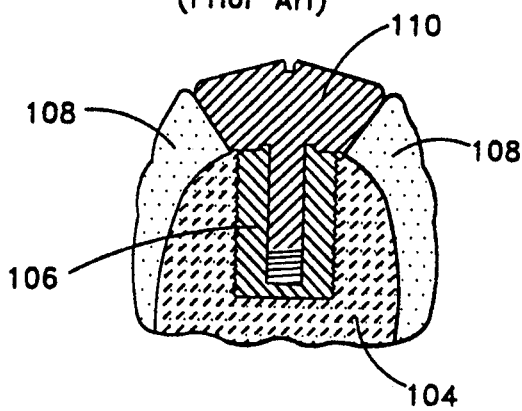
FIG. 1 is a cross-sectional view of a prior art anatomical restoration dental implant system as disclosed in the '111 Patent, showing a healing cap which is threaded onto the implant fixture.
Figure 2:
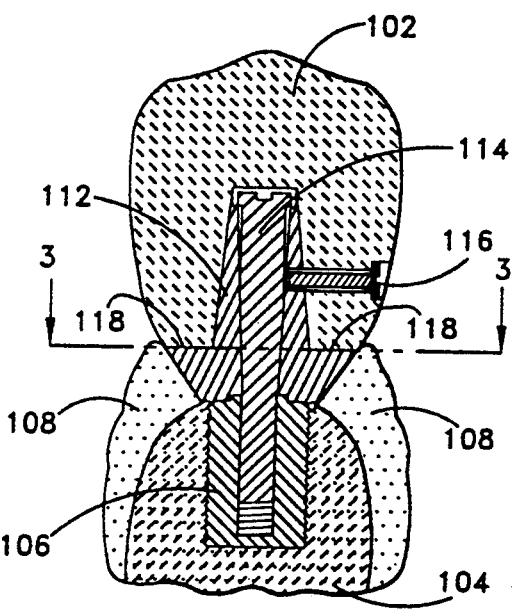
FIG. 2 is also a cross-sectional view of the prior art anatomical restoration dental implant system as disclosed in the '111 Patent, showing an abutment which is threaded onto the implant fixture for supporting a tooth analogue.
Figure 3:
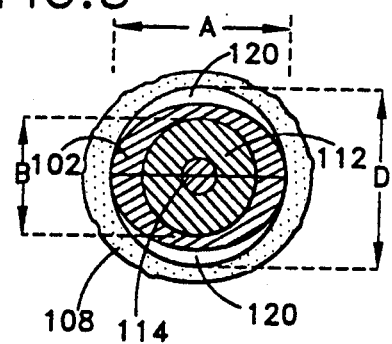
FIG. 3 is a cross-sectional view taken along line 3—3 in FIG. 2.
Figure 5:
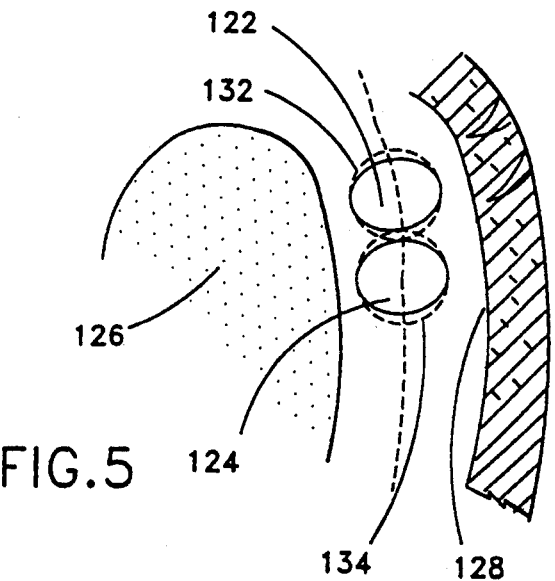
FIG. 5 is an illustrative diagram of a patient's oral cavity, showing the prior art anatomical restoration dental implant system with circular shoulder around the abutment, which may interfere with an adjacent anatomical restoration dental implant system and prevent two tooth analogues from being positioned closely as desired.
Figure 4:
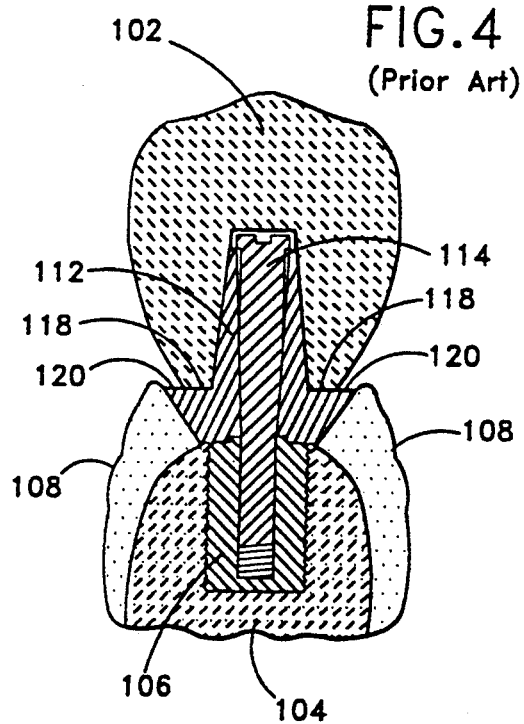
FIG. 4 is another cross-sectional view of the prior art anatomical restoration dental implant system, observed at a 90 degree angle from that of FIG. 3, showing that two opposite narrow spaces are left between the tooth analogue and the gingival tissues because of the mismatching between the elliptical root of the tooth analogue and the circular shoulder around the abutment.
Figure 18:
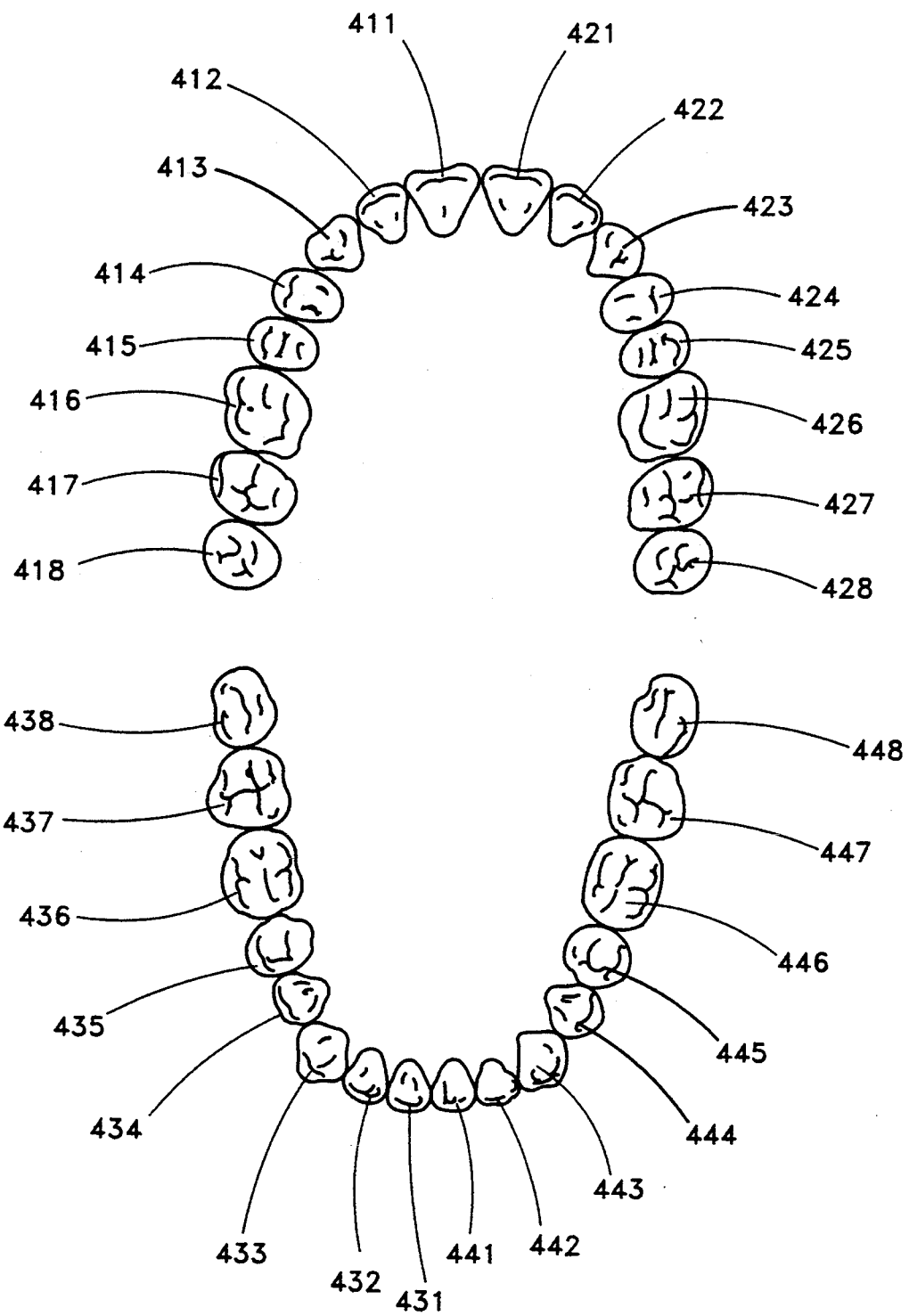
FIG. 18 is an illustrative diagram showing the various shapes of different teeth.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIG. 6, there is shown a perspective view of the present invention healing cap assembly 200, including a bolt member 202 and an elliptical healing cap member 204. The bolt member 202 and the elliptical healing cap member 204 are interlockable.

Referring now to FIG. 6, there is illustrated a perspective view of the bolt member 202. The bolt member 202 has a widened head segment 210 and an elongated shaft segment 220. The widened head segment 210 is disc shaped with a top notch 212 to accommodate a driving tool such as a screw driver for rotating the bolt member 202. The shaft segment 220 has a proximal end 222 and a distal end 224, where the head segment 210 is integrally connected to the distal end 224 of the shaft segment 220. The shaft segment 220 further includes a proximal section 226 and a distal section 228. The proximal section 226 has outer screw threads 230 which are compatible with the inner screw threads of the hollow portion of the implant fixture, whereas the distal section 228 is smooth and has no screw threads.

Referring now to FIGS. 6, 7 and 8, where FIG. 6 is a perspective view of the elliptical healing cap member 204, FIG. 7 is a cross-sectional view of the elliptical healing cap member 204, and FIG. 8 is a top view of the elliptical healing cap member 204. The healing cap member 204 has a divergent body 240 which has a smaller proximal end 242 and a larger distal end 244. The smaller proximal end 242 is circular shaped, whereas the larger distal end 244 is elliptical shaped and has a long-axis and a short axis. The healing cap member 204 further has a stepped interior bore 250 extending from the distal end 244 to the proximal end 242. The interior bore 250 has a wider proximal section 252 and a narrower distal section 254. The proximal section 252 is smooth, whereas the distal section 254 has inner screw threads 256 which are compatible with the outer screw threads 230 of the proximal section 226 of the shaft segment 220 of the bolt member 202. The interior bore 250 is further widened at the larger distal end 244 of the healing cap member 204 to form a circular socket 258 for receiving the disc shaped head segment 210 of the bolt member 202, such that the head segment 210 of the bolt member 202 is flush with the large distal end 244 when it is seated within the circular socket 256. In addition, on the large distal end 244 of the healing cap member 204, two small indents 260 are provided to accommodate the small tips of a dental tool such as a forceps for orienting the healing cap member 204.

Referring now to FIGS. 9 and 10, which are bottom views of the elliptical healing cap 204, showing the interference feature at the small distal end 242 of the elliptical healing cap 204. At the exposed end of the dental implant fixture, there is typically a slightly raised circumferential lip for facilitating the coupling with other dental components such as a cover screw, an impression coping or a healing cap. The circumferential lip is often hexagonal or circular shaped. FIG. 9 shows one embodiment of the present invention healing cap member 204, where a hexagonal recess 262 is provided at the small proximal end 242 of the healing cap member 204 for matching a complementary hexagonal lip at the exposed end of the dental implant fixture. FIG. 10 shows an alternative embodiment of the present invention healing cap member 204, where a circular recess 264 is provided at the small proximal end 242 of the healing cap member 204 for matching a complementary circular lip at the exposed end of the dental implant fixture.

Referring to FIG. 11, there is shown the interlockable feature of the elliptical healing cap member 204 and the bolt member 202 of the present invention interlockable elliptical healing cap assembly 200. The healing cap member 204 and the bolt member 202 are interlockable by threading the proximal section 226 of the shaft segment 210 of the bolt member 202 into the distal section 254 of the interior bore 250 of the healing cap member 204, since the outer screw threads 230 at the proximal section 226 of the shaft segment 210 of the bolt member 202 are compatible with the inner screw threads 256 at the distal section 254 of the interior bore 250 of the healing cap member 204.

This interlockable feature is a critical advantage of the present invention healing cap assembly over the prior art healing cap assemblies. By having the bolt member 202 and the healing cap member 204 interlocked, the present invention healing cap assembly 200 can be handled together as a unit, which reduces the possibility of either dropping or losing the small bolt member 202 into the patient's oral cavity. It also makes the effort of aligning the bolt member 202 and the healing cap member 204 in a patient's oral cavity easier. It further reduces the possibility of mismatching pairs of different configurations or dimensions of the healing cap assemblies, because the bolt member 202 and the healing cap member 204 can be interlocked and packaged, transported and stored as a single unit.

Referring to FIG. 12, there is shown a perspective view of the present invention interlockable elliptical healing cap assembly 200 as it is assembled in a patient's oral cavity. The disc shaped head segment 210 of the bolt member 202 is seated within the circular socket 258 at the larger distal end 244 of the healing cap member 204, so that the head segment 210 of the bolt member 202 is flush with the large distal end 244 of the healing cap member 204. The threaded proximal section 226 extends out from the small proximal end 242 of the healing cap member 204 for engagement with the dental implant fixture.

Referring now to FIG. 13, which is a cross-sectional view of the present invention anatomical restoration dental implant system showing the elliptical healing cap member 204 secured onto a dental implant fixture 306 by the bolt member 202. It is noted that the shaft segment 220 of the bolt member 202 is longer than the interior bore 250 of the healing cap member 204, so that after the shaft segment 220 of the bolt member 202 extends through the interior bore 250 of the healing cap member 204, there is still a substantial portion of the threaded proximal section 228 of the shaft segment 220 of the bolt member 202, which can be threadably engaged with the implant fixture 306 for fastening the healing cap member 204 to the exposed end of the implant fixture 306.

It is further noted that the outer diameter of the threaded proximal section 226 of the shaft segment 220 of the bolt member 202 is slightly smaller than the inner diameter of the smooth proximal section 252 of the interior bore 250 of the healing cap member 204, and the length of the distal section 228 of the shaft segment 220 of the bolt member 202 is longer than that of the distal section 254 of the interior bore 250 of the healing cap member 204. This feature ensures that after the proximal section 228 of the shaft segment 220 of the bolt member 202 is completely threaded through the distal section 254 of the interior bore 250 of the healing cap member 204, the healing cap member 204 and the bolt member 202 are no longer threadably engaged.

This is another critical feature of the present invention. If the bolt member 202 is threadedly engaged with both the healing cap member 204 and the implant fixture 306, then the threaded relationship between the healing cap member 204 and the bolt member 202 will prevent the adjustment of the orientation of the healing cap member 204 when the bolt member 202 is tightened to the implant fixture 306 because of the threaded cross-engagement. When the bolt member 202 has a threaded relationship with the healing cap member 204 and is threadedly tightened into the implant fixture 306, it applies not only a translational downward force but also a rotational torque to the healing cap member 204. The translational force will act to fasten the healing cap member 204 to the implant fixture 306, but the rotational torque will act to rotate the healing cap member 204 about the implant fixture 306. This will destroy the desired orientation of the healing cap member 204, which is that the long-axis of the elliptical healing cap member 204 is aligned with the general radius direction of the patient's oral cavity. In the present invention, by having the bolt member 202 only threadedly engaged with the implant fixture 306, but not threadedly engaged with the healing cap member 204, when the healing cap assembly 200 is secured on the implant fixture 306, the desired orientation of the healing cap member can be maintained.

Referring to FIG. 14, there is shown a perspective view of a matching abutment member 206 of the present invention. The present invention abutment member 206 matches the elliptical healing cap member 204 of the present invention interlockable elliptical healing cap assembly 200. The abutment member 206 has a proximal bolt segment 270 which is identical to the bolt member 202 of the healing cap assembly 200. The abutment member 206 also has a frusto-conical shaped distal head segment 280. The frusto-conical shaped distal head segment 280 has a larger proximal end 282 integrally connected to the proximal bolt segment 270, and a smaller distal end 284 with a notch to accommodate a driving tool such as a screw driver for rotating the abutment member 206. The frusto-conical shaped distal head segment 280 also has a side screw hole 288 to accommodate a small transverse screw for attaching a tooth analogue.

Referring to FIG. 15, there is shown a perspective view of the matching abutment member 206 attached to the elliptical healing cap member 204 of the interlockable elliptical healing cap assembly 200. Since the proximal bolt segment 270 of the abutment member 206 is identical to the bolt member 202 of the healing cap assembly 200, the abutment member 206 can simply replace the bolt member 202 when it is time to install a tooth analogue.

It is noted that the bolt segment 270 of the bolt member 206 is longer than the interior bore 250 of the healing cap member 204, so that after the bolt segment 270 of the bolt member 206 extends through the interior bore 250 of the healing cap member 204, there is still a substantial portion of a proximal section of the bolt segment 270 of the bolt member 206 which can be threadably engaged with an implant fixture for fastening the healing cap member 204 thereupon.

It is further noted that the large circular proximal end 282 of the frusto-conical shaped distal head segment 280 of the abutment member 206 has a diameter smaller than the short-axis of the elliptical shaped distal end 244 of the healing cap member 204, so that when the abutment member 206 is fully secured on the healing cap member 204 in replacement of the bolt member 202 for supporting a tooth analogue, an elliptical shoulder 300 is created for matching the elliptical root of the tooth analogue.

This elliptical shoulder 300 is also a critical feature of the present invention. This solves the problem of mismatching between the root of the tooth analogue, which is often oval or elliptical, and the round or circular abutment shoulder provided by prior art dental implant systems. The smaller profile of the present invention elliptical shoulder 300 also allows two tooth analogues to be positioned at a desired or required close distance.

Referring to FIGS. 16 and 17, there are shown that the matching abutment member 206 is secured on the elliptical healing cap member 204 for supporting a tooth analogue 302. FIG. 16 is a cross-sectional view of the present invention anatomical restoration dental implant system, whereas FIG. 17 is another cross-sectional view of the present invention anatomical restoration dental implant system, observed at a 90 degree angle from that of FIG. 16.

It can be seen than the oval shaped root of the tooth analogue 302 now matches perfectly with the elliptical shoulder 300 around the abutment member 206. As shown in FIGS. 16 and 17, the oval root of the tooth analogue 302 fully covers the elliptical shoulder 300. There are no longer two opposite narrow spaces left between the tooth analogue 302 and the gingival tissues 308. This solves the problem presented by prior art implant systems with circular abutment shoulders, shortens the period of time required for the gingival tissues 308 to recover and heal around the tooth analogue 302, and eliminates any possibility of having food debris and bacteria collected between the root of the tooth analogue 302 and the gingival tissues 308, which in turn expedites the complete healing of the gingival tissues 308 and reduces the chance of causing any infectious diseases.

Another problem solved by the present invention is the precise spacing between adjacent tooth analogues. In prior art dental implant systems the larger profile of the circular shaped shoulder often prevents two adjacent tooth analogues from being positioned at a desired close distance. This problem is solved by the present invention because the smaller profile of the elliptical shoulder 300 at the conjunction of the healing cap member 204 and the abutment member 206 at the direction perpendicular to the general radius direction of a patient's oral cavity allows two tooth analogues to be positioned at a closer distance.

It is also noted that the since the proximal bolt segment 270 of the abutment member 206 is exactly the same as the bolt member 202, the same interlockable and engagement relationship exists between the abutment member 206 and the healing cap 204. For example, when the abutment member 206 is threadedly engaged with the implant fixture 306, the healing cap member 204 and the abutment member 206 are no longer threadably engaged.

The present invention interlockable healing cap assembly further comprises healing cap members which have a rounded triangle shaped top surface. Referring now to FIGS. 19, 20 and 21, where FIG. 19 is a perspective view of the rounded equilateral triangle shaped healing cap member 504, FIG. 20 is a cross-sectional view of the rounded equilateral triangle shaped healing cap member 504, and FIG. 21 is a top view of the rounded equilateral triangle shaped healing cap member 504. The healing cap member 504 has a divergent body 540 which has a smaller proximal end 542 and a larger distal end 544. The smaller proximal end 542 is circular shaped, whereas the larger distal end 544 is rounded equilateral triangle shaped. The healing cap member 504 further has a stepped interior bore 550 extending from the distal end 544 to the proximal end 542. The interior bore 550 has a wider proximal section 552 and a narrower distal section 554. The proximal section 552 is smooth, whereas the distal section 554 has inner screw threads 556 which are compatible with the outer screw threads 230 of the proximal section 226 of the shaft segment 220 of the bolt member 202 (bolt member 202 is shown in FIG. 6). The interior bore 550 is further widened at the larger distal end 544 of the healing cap member 504 to form a circular socket 558 for receiving the disc shaped head segment 210 of the bolt member 202, such that the head segment 210 of the bolt member 202 can be flush with the large distal end 544 when it is seated within the circular socket 558. In addition, on the large distal end 544 of the healing cap member 504, two small indents 560 are provided to accommodate the small tips of a dental tool such as a forceps for orienting the healing cap member 504.

Particularly referring to FIG. 21, an equilateral triangle circumscribing the top end 544 of the healing cap 504 is shown in dotted lines to illustrate that the top end 544 of the healing cap 504 has a rounded equilateral triangle shape. Referring to FIGS. 20 and 21, by way of example only, the width W1 of the rounded equilateral triangle shaped top end 544 of the healing cap 504 is approximately 6 mm, the depth D1 of the rounded equilateral triangle shaped top end 544 of the healing cap 504 is approximately 7 mm, and the height H1 of the rounded equilateral triangle shaped top end 544 of the healing cap 504 may be 3 mm, 4 mm, 6 mm or 8 mm, depending on the patient's dental profile.

Referring now to FIGS. 22 and 23, there are illustrated bottom views of the rounded equilateral triangle shaped healing cap 504, showing the interference feature at the small distal end 542 of the rounded equilateral triangle shaped healing cap 504. At the exposed end of the dental implant fixture, there is typically a slightly raised circumferential lip for facilitating the coupling with other dental components such as a cover screw, an impression coping or a healing cap. The circumferential lip is often hexagonal or circular shaped. FIG. 22 shows one embodiment of the present invention healing cap member 504, where a hexagonal recess 562 is provided at the small proximal end 542 of the healing cap member 504 for matching a complementary hexagonal lip at the exposed end of the dental implant fixture. FIG. 23 shows an alternative embodiment of the present invention healing cap member 504, where a circular recess 564 is provided at the small proximal end 542 of the healing cap member 504 for matching a complementary circular lip at the exposed end of the dental implant fixture.

Referring to FIG. 24, there is shown a perspective view of the matching abutment member 206 attached to the rounded equilateral triangle healing cap member 504 of the interlockable healing cap assembly. Since the proximal bolt segment 270 of the abutment member 206 is identical to the bolt member 202 of the healing cap assembly, the abutment member 206 can simply replace the bolt member 202 when it is time to install a tooth analogue.

It is noted that the bolt segment 270 of the bolt member 206 is longer than the interior bore 550 of the healing cap member 504, so that after the bolt segment 270 of the bolt member 206 extends through the interior bore 550 of the healing cap member 504, there is still a substantial portion of a proximal section of the bolt segment 270 of the bolt member 206 which can be threadably engaged with an implant fixture for fastening the healing cap member 504 thereupon.

It is also noted that a rounded equilateral triangle shaped shoulder 590 is created for matching the rounded equilateral triangle shaped root of the tooth analogue for the upper central incisors 411 and 421. This rounded equilateral triangle shaped shoulder 590 is a critical feature of the present invention because it solves the problem of mismatching between the roots of the central incisors 411 and 421 and the round or circular abutment shoulder provided by prior art dental implant systems. The smaller profile of the present invention rounded equilateral triangle shoulder 590 also allows two tooth analogues to be positioned at a desired or required close distance.

Figure 25:
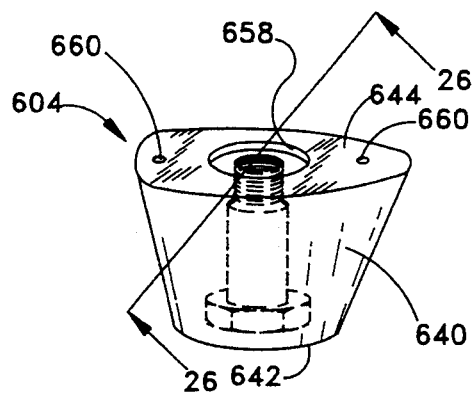
FIG. 25 is a perspective view of the rounded isosceles triangle shaped healing cap member of the present invention interlockable healing cap assembly.
Figure 26:
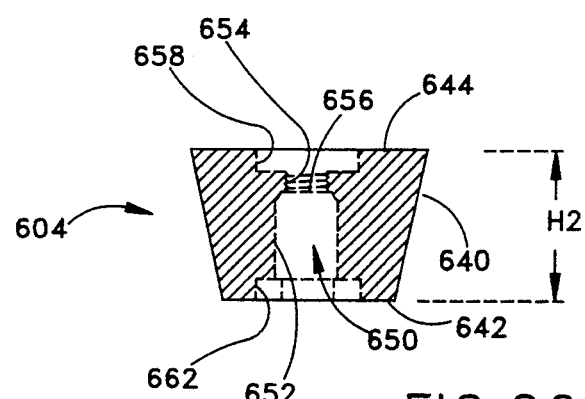
FIG. 26 is a cross-sectional view of the rounded isosceles triangle shaped healing cap member of the present invention interlockable healing cap assembly.
Figure 27:
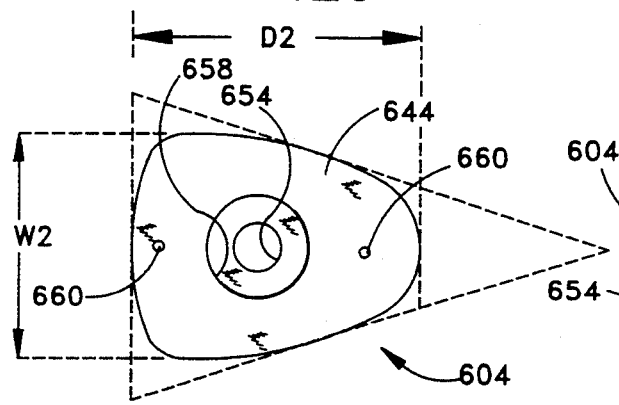
FIG. 27 is a top view of the rounded isosceles triangle shaped healing cap member of the present invention interlockable healing cap assembly.

Referring now to FIGS. 25, 26 and 27, where FIG. 25 is a perspective view of the rounded isosceles triangle shaped healing cap member 604, FIG. 26 is a cross-sectional view of the rounded isosceles triangle shaped healing cap member 604, and FIG. 27 is a top view of the rounded isosceles triangle shaped healing cap member 604. The healing cap member 604 has a divergent body 640 which has a smaller proximal end 642 and a larger distal end 644. The smaller proximal end 642 is circular shaped, whereas the larger distal end 644 is rounded isosceles triangle shaped. The healing cap member 604 further has a stepped interior bore 650 extending from the distal end 644 to the proximal end 642. The interior bore 650 has a wider proximal section 652 and a narrower distal section 654. The proximal section 652 is smooth, whereas the distal section 654 has inner screw threads 656 which are compatible with the outer screw threads 230 of the proximal section 226 of the shaft segment 220 of the bolt member 202 (bolt member 202 is shown in FIG. 6). The interior bore 650 is further widened at the larger distal end 644 of the healing cap member 604 to form a circular socket 658 for receiving the disc shaped head segment 210 of the bolt member 202, such that the head segment 210 of the bolt member 202 can be flush with the large distal end 644 when it is seated within the circular socket 658. In addition, on the large distal end 644 of the healing cap member 604, two small indents 660 are provided to accommodate the small tips of a dental tool such as a forceps for orienting the healing cap member 604.

Particularly referring to FIG. 27, an isosceles triangle circumscribing the top end 644 of the healing cap 604 is shown in dotted lines to illustrate that the top end 644 of the healing cap 604 has a rounded isosceles triangle shape. Referring to FIGS. 26 and 27, by way of example only, the width W2 of the rounded isosceles triangle shaped top end 644 of the healing cap 604 is approximately 5 mm, the depth D2 of the rounded isosceles triangle shaped top end 644 of the healing cap 604 is approximately 6 mm, and the height H2 of the rounded isosceles triangle shaped top end 644 of the healing cap 604 may be 3 mm, 4 mm, 6 mm or 8 mm, depending on the patient's dental profile.

Figure 29:
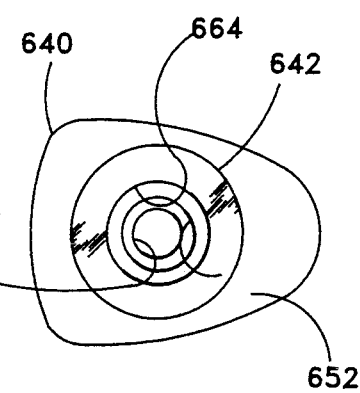
FIG. 29 is a bottom view of an alternative embodiment of the rounded isosceles triangle shaped healing cap member of the present invention interlockable healing cap assembly, showing a round recess for matching with a complementary circular lip on the implant fixture.
Figure 28:
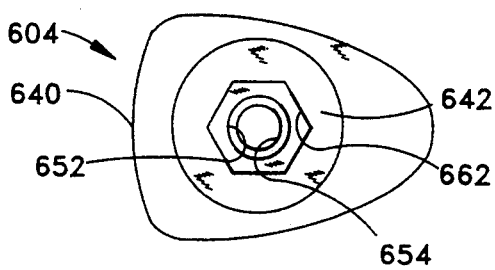
FIG. 28 is a bottom view of the rounded isosceles triangle shaped healing cap member of the present invention interlockable healing cap assembly, showing a hexagonal recess for matching with a complementary hexagonal lip on the implant fixture.

Referring now to FIGS. 28 and 29, which are bottom views of the rounded isosceles triangle shaped healing cap 604, showing the interference feature at the small distal end 642 of the rounded isosceles triangle shaped healing cap 604. At the exposed end of the dental implant fixture, there is typically a slightly raised circumferential lip for facilitating the coupling with other dental components such as a cover screw, an impression coping or a healing cap. The circumferential lip is often hexagonal or circular shaped. FIG. 28 shows one embodiment of the present invention healing cap member 604, where a hexagonal recess 662 is provided at the small proximal end 642 of the healing cap member 604 for matching a complementary hexagonal lip at the exposed end of the dental implant fixture. FIG. 29 shows an alternative embodiment of the present invention healing cap member 604, where a circular recess 664 is provided at the small proximal end 642 of the healing cap member 604 for matching a complementary circular lip at the exposed end of the dental implant fixture.

Figure 30:
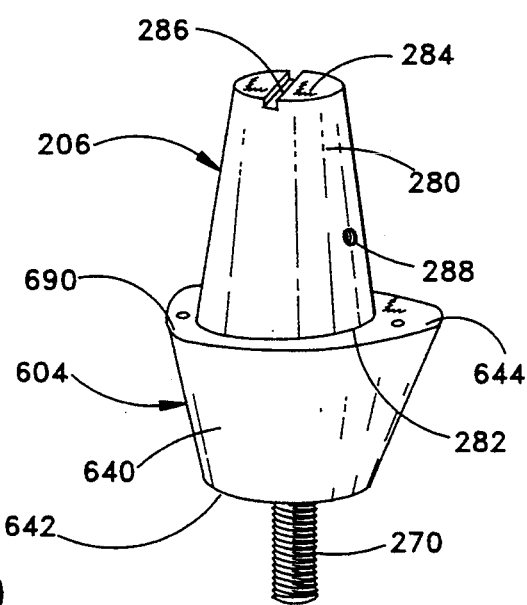
FIG. 30 is a perspective view of the abutment member attached to the rounded isosceles triangle shaped healing cap member of the present invention interlockable healing cap assembly.

Referring to FIG. 30, there is shown a perspective view of the matching abutment member 206 attached to the rounded isosceles triangle healing cap member 604 of the interlockable healing cap assembly. Since the proximal bolt segment 270 of the abutment member 206 is identical to the bolt member 202 of the healing cap assembly, the abutment member 206 can simply replace the bolt member 202 when it is time to install a tooth analogue.

It is noted that the bolt segment 270 of the bolt member 206 is longer than the interior bore 650 of the healing cap member 604, so that after the bolt segment 270 of the bolt member 206 extends through the interior bore 650 of the healing cap member 604, there is still a substantial portion of a proximal section of the bolt segment 270 of the bolt member 206 which can be threadably engaged with an implant fixture for fastening the healing cap member 604 thereupon.

It is further noted that a rounded isosceles triangle shaped shoulder 690 is created for matching the rounded isosceles triangle shaped root of the tooth analogue for the lower lateral incisors 431 and 441, the upper lateral incisors 412 and 422, and the lower lateral incisors 432 and 442. This rounded isosceles triangle shaped shoulder 690 is again a critical feature of the present invention because it solves the problem of mismatching between the roots of the lower lateral incisors 431 and 441, the upper lateral incisors 412 and 422, and the lower lateral incisors 432 and 442, and the round or circular abutment shoulder provided by prior art dental implant systems. The smaller profile of the present invention rounded equilateral triangle shoulder 690 also allows two tooth analogues to be positioned at a desired or required close distance.

The present invention interlockable healing cap assembly additionally comprises healing cap members which have a rounded, particularly circular, shaped top surface. Referring now to FIGS. 31, 32 and 33, where FIG. 31 is a perspective view of a circular shaped healing cap member 704, FIG. 32 is a cross-sectional view of the circular shaped healing cap member 704, and FIG. 33 is a top view of the circular shaped healing cap member 704. The healing cap member 704 has a divergent body 740 which has a smaller proximal end 742 and a larger distal end 744. The smaller proximal end 742 is circular shaped, and the larger distal end 744 is circular shaped. The healing cap member 704 further has a stepped interior bore 750 extending from the distal end 744 to the proximal end 742. The interior bore 750 has a wider proximal section 752 and a narrower distal section 754. The proximal section 752 is smooth, whereas the distal section 754 has inner screw threads 756 which are compatible with the outer screw threads 230 of the proximal section 226 of the shaft segment 220 of the bolt member 202 (bolt member 202 is shown in FIG. 6). The interior bore 750 is further widened at the larger distal end 744 of the healing cap member 704 to form a circular socket 758 for receiving the disc shaped head segment 210 of the bolt member 202, such that the head segment 210 of the bolt member 202 can be flush with the large distal end 744 when it is seated within the circular socket 758. In addition, on the large distal end 744 of the healing cap member 704, two small indents 760 are provided to accommodate the small tips of a dental tool such as a forceps for orienting the healing cap member 704.

Referring now to FIGS. 34 and 35, there are illustrated bottom views of the circular shaped healing cap 704, showing the interference feature at the small distal end 742 of the circular shaped healing cap 704. At the exposed end of the dental implant fixture, there is typically a slightly raised circumferential lip for facilitating the coupling with other dental components such as a cover screw, an impression coping or a healing cap. The circumferential lip is often hexagonal or circular shaped. FIG. 34 shows one embodiment of the present invention healing cap member 704, where a hexagonal recess 762 is provided at the small proximal end 742 of the healing cap member 704 for matching a complementary hexagonal lip at the exposed end of the dental implant fixture. FIG. 35 shows an alternative embodiment of the present invention healing cap member 704, where a circular recess 764 is provided at the small proximal end 742 of the healing cap member 704 for matching a complementary circular lip at the exposed end of the dental implant fixture.

Referring to FIG. 36, there is shown a perspective view of the matching abutment member 206 attached to the circular shaped healing cap member 704 of the interlockable healing cap assembly. Since the proximal bolt segment 270 of the abutment member 206 is identical to the bolt member 202 of the healing cap assembly, the abutment member 206 can simply replace the bolt member 202 when it is time to install a tooth analogue.

It is noted that the bolt segment 270 of the bolt member 206 is longer than the interior bore 750 of the healing cap member 704, so that after the bolt segment 270 of the bolt member 206 extends through the interior bore 750 of the healing cap member 704, there is still a substantial portion of a proximal section of the bolt segment 270 of the bolt member 206 which can be threadably engaged with an implant fixture for fastening the healing cap member 704 thereupon. In addition, a shoulder 790 is created when the bolt member 206 is attached to the healing cap member 704.

Defined in detail, the present invention is an anatomical restoration dental implant system implantable in the gingival tissue and the alveolus of the jaw bone, comprising:

(a) a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;

(b) means for sealing the hollow of the implant fixture during a period after implantation in which the jaw bone is growing about the proximal portion of the implant fixture;

(c) healing cap means for providing a predetermined oval contour to the gingival tissue adjacent the distal end of the implant fixture, such that the gingival tissue re-heals in an oval contour reverse to that of the contour of the healing cap means;

(d) a tooth analogue having a rounded equilateral triangle shaped root;

(e) abutment means for supporting the tooth analogue;

(f) means for securing said tooth analogue to said abutment means;

(g) said healing cap means being an interlockable healing cap assembly, including:

(i) a bolt member having a widened head segment and an elongated shaft segment, the shaft segment having a proximal end and a distal end, and the head segment integrally connected to the distal end of the shaft segment, the shaft segment further having a proximal section and a distal section, the proximal section having outer screw threads compatible with said inner screw threads of said hollow portion of said implant fixture, and the distal section being smooth;

(ii) a healing cap member having a divergent body with a smaller proximal end, a larger distal end, and a stepped interior bore extending from the distal end to the proximal end, the smaller proximal end being circular shaped, the larger distal end being rounded equilateral triangle shaped, and the interior bore having a wide proximal section, and a narrow distal section, the proximal section being smooth, and the distal section having inner screw threads compatible with said outer screw threads of said proximal section of said shaft segment of said bolt member;

(iii) said healing cap member and said bolt member being interlockable by threading said proximal section of said shaft segment of said bolt member into said distal section of said interior bore of said healing cap member;

(iv) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged;

(v) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture;

(h) said abutment means being a matching abutment member further comprising:

(i) a proximal bolt segment being identical to said bolt member of said healing cap assembly;

(ii) a distal frusto-conical shaped head segment having a larger proximal end integrally connected to said proximal bolt segment, and a smaller distal end with means for adapting a driving tool; and (iii) said large proximal end of said distal frusto-conical shaped head segment of said abutment member being circular shaped and smaller than said rounded equilateral triangle shaped distal end of said healing cap member, such that when said abutment member is attached to said healing cap member in replacement of said bolt member for supporting said tooth analogue, a rounded equilateral triangle shaped shoulder is created for matching said rounded equilateral triangle shaped root of said tooth analogue.

Defined alternatively in detail, the present invention is an anatomical restoration dental implant system implantable in the gingival tissue and the alveolus of the jaw bone, comprising:

(a) a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;

(b) means for sealing the hollow of the implant fixture during a period after implantation in which the jaw bone is growing about the proximal portion of the implant fixture;

(c) healing cap means for providing a predetermined oval contour to the gingival tissue adjacent the distal end of the implant fixture, such that the gingival tissue re-heals in an oval contour reverse to that of the contour of the healing cap means;

(d) a tooth analogue having a rounded isosceles triangle shaped root;

(e) abutment means for supporting the tooth analogue;

(f) means for securing said tooth analogue to said abutment means;

(g) said healing cap means being an interlockable healing cap assembly, including:

(i) a bolt member having a widened head segment and an elongated shaft segment, the shaft segment having a proximal end and a distal end, and the head segment integrally connected to the distal end of the shaft segment, the shaft segment further having a proximal section and a distal section, the proximal section having outer screw threads compatible with said inner screw threads of said hollow portion of said implant fixture, and the distal section being smooth;

(ii) a healing cap member having a divergent body with a smaller proximal end, a larger distal end, and a stepped interior bore extending from the distal end to the proximal end, the smaller proximal end being circular shaped, the larger distal end being rounded isosceles triangle shaped, and the interior bore having a wide proximal section, and a narrow distal section, the proximal section being smooth, and the distal section having inner screw threads compatible with said outer screw threads of said proximal section of said shaft segment of said bolt member;

(iii) said healing cap member and said bolt member being interlockable by threading said proximal section of said shaft segment of said bolt member into said distal section of said interior bore of said healing cap member;

(iv) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged;

(v) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture;

(h) said abutment means being a matching abutment member further comprising:

(i) a proximal bolt segment being identical to said bolt member of said healing cap assembly;

(ii) a distal frusto-conical shaped head segment having a larger proximal end integrally connected to said proximal bolt segment, and a smaller distal end with means for adapting a driving tool; and (iii) said large proximal end of said distal frusto-conical shaped head segment of said abutment member being circular shaped and smaller than said rounded isosceles triangle shaped distal end of said healing cap member, such that when said abutment member is attached to said healing cap member in replacement of said bolt member for supporting said tooth analogue, a rounded isosceles triangle shaped shoulder is created for matching said rounded isosceles triangle shaped root of said tooth analogue.

Defined broadly, the present invention is an interlockable healing cap assembly attachable to an anatomical restoration dental implant fixture which is embedded into a patient's jawbone and has an exposed end having a hollow portion with inner screw threads, the healing cap assembly comprising: (a) an integral bolt member having a widened head segment and an elongated shaft segment, the shaft segment having a proximal section with screw threads and a smooth distal section; (b) a healing cap member having a divergent body with a smaller proximal end, a larger distal end, and a stepped interior bore extending from the distal end to the proximal end, the larger distal end having a rounded triangle shape, and the interior bore having a smooth proximal section and a threaded distal section; (c) said healing cap member and said bolt member being interlockable by threading said proximal section of said shaft segment of said bolt member into said distal section of said interior bore of said healing cap member; (d) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged; and (e) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture.

Defined also broadly, the present invention is an interlockable healing cap assembly attachable to an anatomical restoration dental implant fixture which is embedded into a patient's jawbone and has an exposed end having a hollow portion with inner screw threads, the healing cap assembly comprising: (a) an integral bolt member having a widened head segment and an elongated shaft segment, the shaft segment having a proximal section with screw threads and a smooth distal section; (b) a healing cap member having a divergent body with a smaller proximal end, a larger distal end, and a stepped interior bore extending from the distal end to the proximal end, the larger distal end having a rounded shape, and the interior bore having a smooth proximal section and a threaded distal section; (c) said healing cap member and said bolt member being interlockable by threading said proximal section of said shaft segment of said bolt member into said distal section of said interior bore of said healing cap member; (d) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged; and (e) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture.

Defined more broadly, the present invention is a healing cap assembly attachable to an exposed end of a dental implant fixture which has a hollow with inner screw threads, the healing cap assembly comprising: (a) healing cap member having a divergent body with a smaller proximal end, a larger distal end, and an interior bore extending from the distal end to the proximal end, the larger distal end having a non-circular shape; and (b) means for fastening the healing cap member to the exposed end of the dental implant fixture.

Alternatively defined, the present invention is a method for implanting a tooth analogue with rounded triangle shaped root in the gingival tissue and the alveolus of the jawbone in a patient's oral cavity, the method comprising the steps of: (a) implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length; (b) sealing the hollow of the fixture with a cover means during a period after implantation in which the jaw bone is growing about the proximal portion of the fixture and the opened gingival tissue is healing, thereby preventing the jaw bone from entering the fixture; (c) reopening the gingival tissue and replacing said cover means with a healing cap assembly which includes a bolt member and an healing cap member having a divergent body with a smaller proximal end, a larger distal end, and an interior bore extending from the distal end to the proximal end, where the larger distal end is rounded triangle shaped; (d) removing said bolt member and replacing it with a matching abutment member which has a proximal bolt segment identical to said bolt member and a distal frusto-conical shaped head segment having a smaller distal end and a larger proximal end integrally connected to the proximal bolt segment, where the larger proximal end is circular shaped and smaller than said rounded triangle shaped distal end of said healing cap member, such that when the matching abutment member is attached to said healing cap member in replacement of said bolt member for supporting said tooth analogue, a rounded triangle shaped shoulder is created for matching said rounded triangle shaped root of said tooth analogue; and (e) releasibly attaching a tooth analogue to said matching abutment member such that said rounded triangle shaped root of said tooth analogue matches said rounded triangle shaped shoulder created at the conjunction of said healing cap member and said matching abutment member.

Alternatively defined broadly, the present invention is a method of attaching an interlockable healing cap assembly to a component of an anatomical restoration dental implant system, where the dental component has a threaded hollow, the method comprising the steps of: (a) utilizing a bolt member which has a smooth distal section and a threaded proximal section engagable with said threaded hollow of said dental component; (b) utilizing a healing cap member which has a divergent body with a smaller proximal end, a larger distal end, and an interior bore having a threaded distal section offset from said threaded proximal section of said bolt member, and a smooth proximal section offset from said smooth distal section of said bolt member; (c) interlocking said healing cap member and said bolt member by threading said threaded proximal section of said bolt member into said threaded distal section of said interior bore of said healing cap member; (d) attaching said healing cap member with said interlocked bolt member onto said dental component; and (e) fastening said healing cap member to said dental component by threading said bolt member until its threaded proximal section is completely disengaged with said threaded distal section of said healing cap member, and instead engaged with said threaded hollow of said dental component.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An anatomical restoration dental implant system implantable in the gingival tissue and the alveolus of the jaw bone, comprising:
   a. a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along a portion of its length;
   b. means for sealing the hollow of the implant fixture during a period after implantation in which the jaw bone is growing about the proximal portion of the implant fixture;
   c. healing cap means for providing a predetermined oval contour to the gingival tissue adjacent the distal end of the implant fixture, such that the gingival tissue re-heals in an oval contour which conforms to the contour of the healing cap means;
   d. a tooth analogue having a rounded equilateral triangle shaped root;
   e. abutment means for supporting the tooth analogue;
   f. means for securing said tooth analogue to said abutment means;
   g. said healing cap means being an interlockable healing cap assembly, including:
      (i) a bolt member having a widened head segment and an elongated shaft segment, the shaft segment having a proximal end and a distal end, and the head segment integrally connected to the distal end of the shaft segment, the shaft segment further having a proximal section and a distal section, the proximal section having outer screw threads compatible with said inner screw threads of said hollow portion of said implant fixture, and the distal section being smooth,
      (ii) a healing cap member having a divergent body with a smaller proximal end, a larger distal end, and a stepped interior bore extending from the distal end of the healing cap member to the proximal end of the healing cap member, the smaller proximal end being circular shaped, the larger distal end being rounded equilateral triangle shaped, and the interior bore having a wide proximal section, and a narrow distal section, the proximal section of the interior bore being smooth, and the distal section of the interior bore having inner screw threads compatible with said outer screw threads of said proximal section of said shaft segment of said bolt member,
      (iii) said healing cap member and said bolt member being interlockable by threading said proximal section of said shaft segment of said bolt member into said distal section of said interior bore of said healing cap member,
      (iv) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged, (v) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture;

h. said abutment means being a matching abutment member further comprising:
   (i) a proximal bolt segment being identical to said bolt member of said healing cap assembly,
   (ii) a distal frusto-conical shaped head segment having a larger proximal end integrally connected to said proximal bolt segment, and a smaller distal end with means for adapting a driving tool, and
   (iii) said large proximal end of said distal frusto-conical shaped head segment of said abutment member being circular shaped and smaller than said rounded equilateral triangle shaped distal end of said healing cap member, such that when said abutment member is attached to said healing cap member in replacement of said bolt member for supporting said tooth analogue, a rounded equilateral triangle shaped shoulder is created for matching said rounded equilateral triangle shaped root of said tooth analogue.

2. The invention as defined in claim 1 wherein said larger distal end of said healing cap member further comprises a widened socket for adapting said widened head segment of said bolt member such that when said healing cap assembly is attached to said implant fixture, the tip of the head segment of the bolt member lies flush with the larger distal end of the healing cap member.

3. The invention as defined in claim 1 wherein said larger distal end of said healing cap member further comprises means adaptable with a dental tool for orienting said healing cap member.

4. The invention as defined in claim 3 wherein said means adaptable with a dental tool for orienting said healing cap member includes two small indents located on said larger distal end of said healing cap member.

5. The invention as defined in claim 1 wherein said head segment of said bolt member has means cooperable with a driving tool.

6. The invention as defined in claim 5 wherein said means cooperable with a driving tool includes a top notch located at said head segment of said bolt member.

7. The invention as defined in claim 1 further comprising a mating interface at said exposed end of said implant fixture and a complementary mating interface at said proximal end of said healing cap member for orienting and aligning said healing cap assembly.

8. The invention as defined in claim 7 wherein said mating interface at said exposed end of said implant fixture is a hexagonal lip and said complementary mating interface at said proximal end of said healing cap member is a hexagonal recess.

9. The invention as defined in claim 7 wherein said mating interface at said exposed end of said implant fixture is a circular lip and said complementary mating interface at said proximal end of said healing cap member is a circular recess.

10. An anatomical restoration dental implant system implantable in the gingival tissue and the alveolus of the jaw bone, comprising:

a. a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;

b. means for sealing the hollow of the implant fixture during a period after implantation in which the jaw bone is growing about the proximal portion of the implant fixture;

c. healing cap means for providing a predetermined oval contour to the gingival tissue adjacent the distal end of the implant fixture, such that the gingival tissue re-heals in an oval contour which conforms to the contour of the healing cap means;

d. a tooth analogue having a rounded isosceles triangle shaped root;

e. abutment means for supporting the tooth analogue;

f. means for securing said tooth analogue to said abutment means;

g. said healing cap means being an interlockable healing cap assembly, including:
   (i) a bolt member having a widened head segment and an elongated shaft segment, the shaft segment having a proximal end and a distal end, and the head segment integrally connected to the distal end of the shaft segment, the shaft segment further having a proximal section and a distal section, the proximal section having outer screw threads compatible with said inner screw threads of said hollow portion of said implant fixture, and the distal section being smooth,
   (ii) a healing cap member having a divergent body with a smaller proximal end, a larger distal end, and a stepped interior bore extending from the distal end of the healing cap member to the proximal end of the healing cap member, the smaller proximal end being circular shaped, the larger distal end being rounded isosceles triangle shaped, and the interior bore having a wide proximal section, and a narrow distal section, the proximal section of the interior bore being smooth, and the distal section of the interior bore having inner screw threads compatible with said outer screw threads of said proximal section of said shaft segment of said bolt member,
   (iii) said healing cap member and said bolt member being interlockable by threading said proximal section of said shaft segment of said bolt member into said distal section of said interior bore of said healing cap member,
   (iv) said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged, (v) said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture;

(h) said abutment means being a matching abutment member further comprising:

(i) a proximal bolt segment being identical to said bolt member of said healing cap assembly, (ii) a distal frusto-conical shaped head segment having a larger proximal end integrally connected to said proximal bolt segment, and a smaller distal end with means for adapting a driving tool, and (iii) said large proximal end of said distal frusto-conical shaped head segment of said abutment member being circular shaped and smaller than said rounded isosceles triangle shaped distal end of said healing cap member, such that when said abutment member is attached to said healing cap member in replacement of said bolt member for supporting said tooth analogue, a rounded isosceles triangle shaped shoulder is created for matching said rounded isosceles triangle shaped root of said tooth analogue.

11. The invention as defined in claim 10 wherein said larger distal end of said healing cap member further comprises a widened socket for adapting said widened head segment of said bolt member such that when said healing cap assembly is attached to said implant fixture, the tip of the head segment of the bolt member lies flush with the larger distal end of the healing cap member.

12. The invention as defined in claim 10 wherein said larger distal end of said healing cap member further comprises means adaptable with a dental tool for orienting said healing cap member.

13. The invention as defined in claim 12 wherein said means adaptable with a dental tool for orienting said healing cap member includes two small indents located on said larger distal end of said healing cap member.

14. The invention as defined in claim 10 wherein said head segment of said bolt member has means cooperable with a driving tool.

15. The invention as defined in claim 14 wherein said means cooperable with a driving tool includes a top notch located at said head segment of said bolt member.

16. The invention as defined in claim 10 further comprising a mating interface at said exposed end of said implant fixture and a complementary mating interface at said proximal end of said healing cap member for orienting and aligning said healing cap assembly.

17. The invention as defined in claim 16 wherein said mating interface at said exposed end of said implant fixture is a hexagonal lip and said complementary mating interface at said proximal end of said healing cap member is a hexagonal recess.

18. The invention as defined in claim 16 wherein said mating interface at said exposed end of said implant fixture is a circular lip and said complementary mating interface at said proximal end of said healing cap member is a circular recess.

19. An interlockable healing cap assembly attachable to an anatomical restoration dental implant fixture which is embedded into a patient's jawbone and has an exposed end having a hollow portion with inner screw threads, the healing cap assembly comprising:

a. an integral bolt member having a widened head segment and an elongated shaft segment, the shaft segment having a proximal section with screw threads and a smooth distal section;

b. a healing cap member having a divergent body with a smaller proximal end, a larger distal end, and a stepped interior bore extending from the distal end to the proximal end, the larger distal end having a rounded triangle shape, and the interior bore having a smooth proximal section and a threaded distal section;

c. said healing cap member and said bolt member being interlockable by threading said proximal section of said shaft segment of said bolt member into said distal section of said interior bore of said healing cap member;

d. said distal section of said shaft segment of said bolt member being longer than said distal section of said interior bore of said healing cap member, such that after said proximal section of said shaft segment of said bolt member is completely threaded through said distal section of said interior bore of said healing cap member from said distal end of said healing cap member, said healing cap member and said bolt member are no longer threadably engaged; and e. said shaft segment of said bolt member being longer than said interior bore of said healing cap member, such that after said shaft segment of said bolt member extends through said interior bore of said healing cap member from said distal end of said healing cap member, there is still a substantial portion of said proximal section of said shaft segment of said bolt member which can be threadably engaged with said implant fixture for fastening said healing cap member to said exposed end of said implant fixture.

20. The invention as defined in claim 19 wherein said rounded triangle shape is a rounded equilateral triangle shape.

21. The invention as defined in claim 19 wherein said rounded triangle shape is a rounded isosceles triangle shape.

22. The invention as defined in claim 19 wherein said larger distal end of said healing cap member further comprises a widened socket for adapting said widened head segment of said bolt member such that when said healing cap assembly is attached to said implant fixture, the tip of the head segment of the bolt member lies flush with the larger distal end of the healing cap member, and the larger distal end of said healing cap member further comprises two opposite indents adaptable with a dental forceps for orienting said healing cap member.

23. The invention as defined in claim 19 wherein said head segment of said bolt member has means cooperable with a driving tool.

24. The invention as defined in claim 19 further comprising mating means for aligning said healing cap member with said implant fixture.

25. The invention as defined in claim 19 further comprising a matching abutment member for supporting a tooth analogue with a rounded triangle shaped root, the abutment member having:
   a. a proximal bolt segment being identical to said bolt member of said healing cap assembly;
   b. a distal frusto-conical shaped head segment having a larger proximal end integrally connected to said proximal bolt segment, and a smaller distal end with means for adapting a driving tool; and
   c. said large proximal end of said distal frusto-conical shaped head segment of said abutment member being circular shaped and smaller than said rounded triangle shaped distal end of said healing cap member, such that when said abutment member is attached to said healing cap member in replacement of said bolt member for supporting said tooth analogue, a rounded triangle shaped shoulder is created for matching said rounded triangle shaped root of said tooth analogue.

26. A method for implanting a tooth analogue with rounded triangle shaped root in the gingival tissue and the alveolus of the jawbone in a patient's oral cavity, the method comprising the steps of:
   a. implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length;
   b. sealing the hollow of the fixture with a cover means during a period after implantation in which the jaw bone is growing about the proximal portion of the fixture and the opened gingival tissue is healing, thereby preventing the jaw bone from entering the fixture;
   c. reopening the gingival tissue and replacing said cover means with a healing cap assembly which includes a bolt member and a healing cap member having a divergent body with a smaller proximal end, a larger distal end, and an interior bore extending from the distal end to the proximal end, where the larger distal end is rounded triangle shaped;
   d. removing said bolt member and replacing it with a matching abutment member which has a proximal bolt segment identical to said bolt member and a distal frusto-conical shaped head segment having a smaller distal end and a larger proximal end integrally connected to the proximal bolt segment, where the larger proximal end is circular shaped and smaller than said rounded triangle shaped distal end of said healing cap member, such that when the matching abutment member is attached to said healing cap member in replacement of said bolt member for supporting said tooth analogue, a rounded triangle shaped shoulder is created for matching said rounded triangle shaped root of said tooth analogue; and releasibly attaching said tooth analogue having a rounded triangle shaped root to said matching abutment member such that said rounded triangle shaped root of said tooth analogue matches said rounded triangle shaped shoulder created at the conjunction of said healing cap member and said matching abutment member.

27. The invention as defined in claim 26 further comprising the steps of orienting said healing cap member in said patient's oral cavity, and securing said healing cap member with said bolt member for providing a predetermined contour to the healing gingival tissue adjacent the implant fixture.

28. The invention as defined in claim 26 further comprising the step of interlocking said healing cap member with said bolt member before said healing cap member is secured on said implant fixture by providing screw threads at a narrow distal portion of said interior bore of said healing cap member while keeping a proximal portion of said interior bore smooth.

29. The invention as defined in claim 26 further comprising the step of coupling said healing cap member with said implant fixture by providing a mating interface at said exposed end of said implant fixture and a complementary mating interface at said proximal end of said healing cap member.

* * * * *